(12) United States Patent
Nawaz et al.

(10) Patent No.: US 9,969,667 B2
(45) Date of Patent: May 15, 2018

(54) SYSTEMS AND METHODS RELATED TO THE PRODUCTION OF METHYL TERT-BUTYL ETHER

(71) Applicant: SABIC Global Technologies B.V., Bergen op Zoom (NL)

(72) Inventors: Zeeshan Nawaz, Riyadh (SA); Ali Al-Hammad, Riyadh (SA); Talal Al-Shammari, Riyadh (SA); Shehzada Khurram, Riyadh (SA); Khalid Karim, Riyadh (SA); Mubarik Ali Bashir, Riyadh (SA); Thabet Al-Qahtani, Riyadh (SA); Abdullah Turki Al-Jaloud, Riyadh (SA); Saud Al-Khudeer, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days. days.

(21) Appl. No.: 15/551,397

(22) PCT Filed: Feb. 16, 2016

(86) PCT No.: PCT/IB2016/050824
§ 371 (c)(1),
(2) Date: Aug. 16, 2017

(87) PCT Pub. No.: WO2016/132292
PCT Pub. Date: Aug. 25, 2016

(65) Prior Publication Data
US 2018/0044271 A1    Feb. 15, 2018

Related U.S. Application Data

(60) Provisional application No. 62/118,152, filed on Feb. 19, 2015.

(51) Int. Cl.
*C07C 41/06* (2006.01)
*C07C 43/04* (2006.01)

(52) U.S. Cl.
CPC ............ *C07C 41/06* (2013.01); *C07C 43/046* (2013.01); *B01J 2219/00006* (2013.01)

(58) Field of Classification Search
CPC ......... C07C 41/42; C07C 43/046; C07C 9/10; B01J 2219/00006; B01J 19/245; B01J 2219/24; B01J 2219/2401
See application file for complete search history.

(56) References Cited

U.S. PATENT DOCUMENTS 3,914,332 A    10/1975    Dickason
4,088,671 A    5/1978     Kobylinski
(Continued)

FOREIGN PATENT DOCUMENTS

EP    0605822    7/1994
FR    2594139    8/1987

OTHER PUBLICATIONS

Sanfilippo, D., et al. "Fluidized bed reactors for paraffins dehydrogenation." Chem Eng Sci. 1992; 47(9-11): 2313-8.
(Continued)

*Primary Examiner* — Jafar Parsa
(74) *Attorney, Agent, or Firm* — Ballard Spahr LLP

(57) ABSTRACT

Disclosed herein is a system comprising: a) a Fischer-Tropsch reactor comprising a first inlet and a first outlet; b) an olefin separator comprising a second inlet and a second outlet; c) a deisobutanizer comprising a third inlet and a third outlet; d) an iso-butane to isobutylene reactor comprising a fourth inlet and a fourth outlet; and e) a MTBE reactor comprising a fifth inlet, the recited structures are in fluid communication.

20 Claims, 1 Drawing Sheet

(56) References Cited

U.S. PATENT DOCUMENTS

| | | | |
|---|---|---|---|
| 4,207,248 | A | 6/1980 | Butter et al. |
| 5,069,794 | A | 12/1991 | Haag et al. |
| 5,414,147 | A | 5/1995 | Koga |
| 6,156,950 | A | 12/2000 | Ragil et al. |
| 6,338,791 | B1 | 1/2002 | Ragil et al. |
| 6,818,333 | B2 | 11/2004 | Chau et al. |
| 7,364,650 | B2 | 4/2008 | Font Freide |
| 7,417,173 | B2 | 8/2008 | Crone et al. |
| 7,638,675 | B2 | 12/2009 | Shecterle et al. |
| 7,855,234 | B2 | 12/2010 | Hoek et al. |
| 2013/0062253 | A1 | 3/2013 | Timken |
| 2013/0224808 | A1 | 8/2013 | Bell et al. |

OTHER PUBLICATIONS

International Search Report and Written Opinion dated Apr. 21, 2016 by the International Searching Authority for International Application No. PCT/IB2016/050824, which was filed on Feb. 16, 2016 and published as WO 2016/132292 on Aug. 25, 2016 (Applicant—SABIC Global Technologies B.V.) (9 pages).

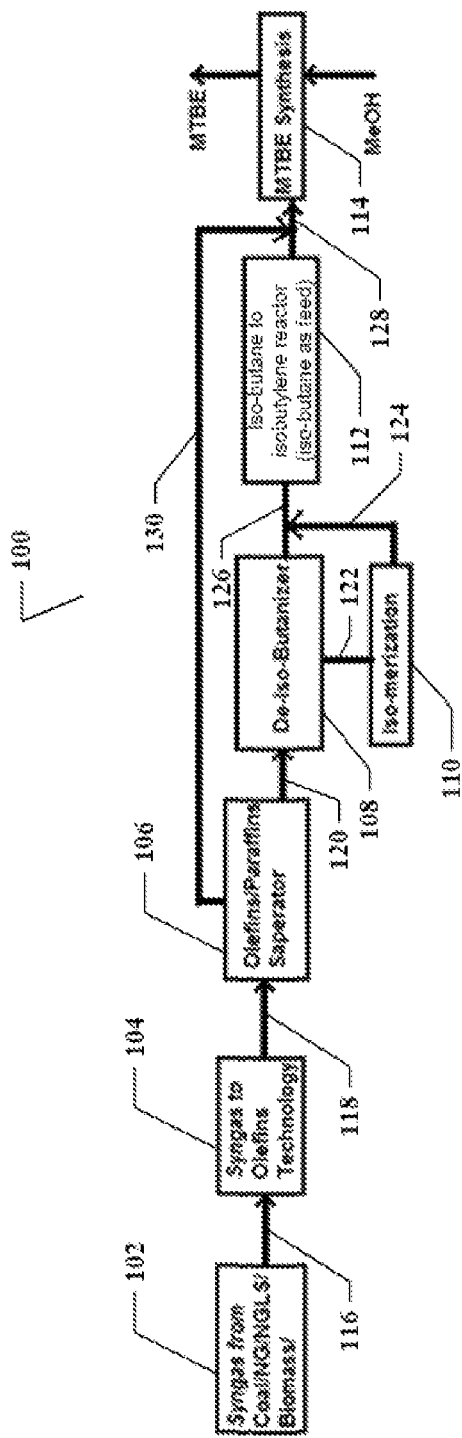

SYSTEMS AND METHODS RELATED TO THE PRODUCTION OF METHYL TERT-BUTYL ETHER

CROSS-REFERENCE TO RELATED APPLICATIONS

This is a U.S. National Phase Application of International Application No. PCT/IB2016/050824, filed Feb. 16, 2016, which claims the benefit of U.S. Provisional Application No. 62/118,152, filed Feb. 19, 2015, which are both incorporated herein by reference in their entirety.

BACKGROUND

Methyl tert-butyl ether (MTBE) is well recognized as a gasoline blending component. MTBE (methyl tertiary-butyl ether) is a chemical compound that is typically manufactured by the chemical reaction of methanol and isobutylene. MTBE is produced in very large quantities (over 200,000 barrels per day in the U.S. in 1999) and is almost exclusively used as a fuel additive in motor gasoline. It is one of a group of chemicals commonly known as "oxygenates" because they raise the oxygen content of gasoline. At room temperature, MTBE is a volatile, flammable, and colorless liquid that dissolves rather easily in water. The use of MTBE in the production of gasoline for the protection of the environment and octane improvement has made it the fastest growing large volume chemical in the world.

Syngas (mixtures of $H_2$ and CO) can be readily produced from either coal or methane (natural gas) by methods well known in the art and widely commercially practiced around the world. A number of well-known industrial processes use syngas for producing various oxygenated organic chemicals. The Fischer-Tropsch catalytic process for catalytically producing hydrocarbons from syngas was initially discovered and developed in the 1920's, and was used in South Africa for many years to produce gasoline range hydrocarbons as automotive fuels. The catalysts typically comprises iron or cobalt supported on alumina or titania. Promoters, such as, rhenium, zirconium, manganese, and the like, can sometimes be used with cobalt catalysts, to improve various aspects of catalytic performance. The products were typically gasoline-range hydrocarbon liquids having six or more carbon atoms, along with heavier hydrocarbon products.

Today lower molecular weight C1-05 hydrocarbons (paraffins and/or olefins) are desired and can be obtained from syngas gas via Fischer-Tropsch catalytic process. There is a need to convert the paraffins and/or olefins obtained into other useful compound(s).

Accordingly, there remains a long-term market need for new and improved methods for producing useful compound(s) from low molecular weight C1-C5 hydrocarbons, such as from C4 hydrocarbons, from non-petroleum feedstocks.

Accordingly, a system and a method useful for the production of MTBE are described herein.

SUMMARY OF THE INVENTION

Disclosed herein is a system comprising: a) a Fischer-Tropsch reactor comprising a first inlet and a first outlet; b) an olefin separator comprising a second inlet and a second outlet; c) a deisobutanizer comprising a third inlet and a third outlet; d) an iso-butane to isobutylene reactor comprising a fourth inlet and a fourth outlet; and e) a MTBE reactor comprising a fifth inlet, wherein the Fischer-Tropsch reactor is in fluid communication with the olefin separator via a first connector, wherein the first connector is connected to the first outlet of the Fischer-Tropsch reactor and to the second inlet of the olefin separator, wherein the olefin separator is in fluid communication with the deisobutanizer via a second connector, wherein the second connector is connected to the second outlet of the olefin separator and to the third inlet of the deisobutanizer, wherein the deisobutanizer is in fluid communication with the iso-butane to isobutylene reactor via a third connector, wherein the third connector is connected to the third outlet of the deisobutanizer and to the fourth inlet of the iso-butane to isobutylene reactor, wherein the iso-butane to isobutylene reactor is in fluid communication with the MTBE reactor via a fourth connector, wherein the fourth connector is connected to the fourth outlet of the iso-butane to isobutylene reactor and to the fifth inlet of the MTBE reactor.

Also disclosed herein is a method comprising the steps of: a) providing a first product gas stream comprising at least about 1 wt % of a first C4 hydrocarbon product, wherein the first C4 hydrocarbon product comprises a C4 olefin hydrocarbon product comprising isobutylene and a C4 paraffin hydrocarbon product, wherein the C4 paraffin hydrocarbon product comprises n-butane and i-butane; b) separating at least a portion of the C4 olefin hydrocarbon product comprising isobutylene from the first C4 hydrocarbon product, thereby producing a second C4 hydrocarbon product; c) separating at least a portion of the n-butane from the second C4 hydrocarbon product, thereby producing a third C4 hydrocarbon product; d) isomerizing at least a portion of the separated n-butane into i-butane; e) combining at least a portion of the i-butane produced in step d) with the third C4 hydrocarbon product, thereby producing a fourth C4 hydrocarbon product; f) producing isobutylene from at least a portion of the fourth C4 hydrocarbon product; g) combining at least a portion of the separated C4 olefin hydrocarbon product comprising isobutylene and at least a portion of the isobutylene produced in step f), thereby producing a fifth C4 hydrocarbon product; and h) producing methyl tert-butyl ether (MTBE) from at least a portion of the fifth C4 hydrocarbon product.

Additional advantages will be set forth in part in the description which follows, and in part will be obvious from the description, or can be learned by practice of the aspects described below. The advantages described below will be realized and attained by means of the chemical compositions, methods, and combinations thereof particularly pointed out in the appended claims. It is to be understood that both the foregoing general description and the following detailed description are exemplary and explanatory only and are not restrictive.

DESCRIPTION OF THE FIGURES

The accompanying FIGURES, which are incorporated in and constitute a part of this specification, illustrate several aspects, and together with the description, serve to explain the principles of the invention.

FIG. 1 shows a flow diagram of a system and a method disclosed herein.

Additional advantages of the invention will be set forth in part in the description that follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Disclosed herein are materials, compounds, compositions, and components that can be used for, can be used in conjunction with, can be used in preparation for, or are products of the disclosed method and compositions. It is to be understood that when combinations, subsets, interactions, groups, etc. of these materials are disclosed that while specific reference of each various individual and collective combinations and permutation of these compounds cannot be explicitly disclosed, each is specifically contemplated and described herein. For example, if a catalyst component is disclosed and discussed, and a number of alternative solid state forms of that component are discussed, each and every combination and permutation of the catalyst component and the solid state forms that are possible are specifically contemplated unless specifically indicated to the contrary. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

1. Definitions

In this specification and in the claims which follow, reference will be made to a number of terms which shall be defined to have the following meanings:

It must be noted that, as used in the specification and the appended claims, the singular forms "a," "an" and "the" include plural referents unless the context clearly dictates otherwise. Thus, for example, reference to "a hydrocarbon" includes mixtures of hydrocarbons.

Ranges can be expressed herein as from one particular value, and/or to another particular value. When such a range is expressed, another aspect includes from the one particular value and/or to the other particular value. Similarly, when values are expressed as approximations, by use of the antecedent "," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such a ratio regardless of whether additional components are contained in the compound.

A weight percent of a component, unless specifically stated to the contrary, is based on the total weight of the formulation or composition in which the component is included.

2. Fischer-Tropsch Catalytic Process

The Fischer-Tropsch catalytic process for producing hydrocarbons from syngas is known in the art. Several reactions can take place in a Fischer-Tropsch process, such as, a Fischer-Tropsch (FT) reaction, a water gas shift reaction, and a hydrogen methanation, as shown in Scheme 1.

Scheme 1

FT reaction:

Water Gas Shift Reaction (WGS):
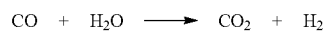

Methanation
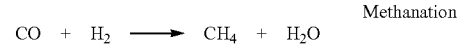

The gases that are being mixed in the Fischer-Tropsch process described herein comprise $H_2$ and CO. The $H_2$/CO molar ratio of the feed gas can be from 0.5 to 4. For example, the $H_2$/CO molar ratio can be from 1.0 to 3.0, such as, for example, from 1.5 to 3.0, or in another example, from 1.5 to 2.5. It will be appreciated that the $H_2$/CO molar ratio can control the selectivity of the hydrocarbons that are being produced. The consumption molar ratio of $H_2$/CO is usually from about 1.0 to about 2.5, such as for example, from about 1.5 to 2.1. This ratio increases as long as the water gas shift reaction is active and, thus, the use of a feed ratio below the consumption ratio will result in a stable $H_2$/CO ratio during the reaction within an acceptable range (normally below 2). The $H_2$ and CO are catalytically reacted in a Fischer-Tropsch reaction.

A Fischer-Tropsch process that targets the production of olefins (C2-C10 olefins) is desired and such process can produce a significant amount of C4 hydrocarbons, including C4 paraffins and C4 olefins. As disclosed herein, a stream comprising C4 hydrocarbons can undergo processing to produce MTBE, which can be used as a gasoline additive to raise the octane number of the gasoline. The system and method disclosed herein are capable of producing MTBE from a gas product stream produced in a Fischer-Tropsch Process.

MTBE has the chemical structure $(CH_3)_3COCH_3$ and is a volatile, flammable, and colorless liquid.

3. System

Disclosed herein is a system comprising: a) a Fischer-Tropsch reactor comprising a first inlet and a first outlet; b) an olefin separator comprising a second inlet and a second outlet; c) a deisobutanizer comprising a third inlet and a third outlet; d) an iso-butane to isobutylene reactor comprising a fourth inlet and a fourth outlet; and e) a MTBE reactor comprising a fifth inlet, wherein the Fischer-Tropsch reactor is in fluid communication with the olefin separator via a first connector, wherein the first connector is connected to the first outlet of the Fischer-Tropsch reactor and to the second inlet of the olefin separator, wherein the olefin separator is in fluid communication with the deisobutanizer via a second connector, wherein the second connector is connected to the second outlet of the olefin separator and to the third inlet of the deisobutanizer, wherein the deisobutanizer is in fluid communication with the iso-butane to isobutylene reactor via a third connector, wherein the third connector is connected to the third outlet of the deisobutanizer and to the fourth inlet of the iso-butane to isobutylene reactor, wherein the iso-butane to isobutylene reactor is in fluid communication with the MTBE reactor via a fourth connector, wherein the fourth connector is connected to the fourth outlet of the iso-butane to isobutylene reactor and to the fifth inlet of the MTBE reactor.

It is understood that the sequence of reactors disclosed herein can vary based on the product distribution in the Fischer-Tropsch process, which produces olefins from syngas.

In one aspect, the system further comprises an isomerization reactor comprising a sixth inlet and a sixth outlet, wherein the deisobutanizer further comprises a seventh outlet, wherein the isomerization reactor is in fluid communication with the deisobutanizer via fifth connector, wherein fifth connector is connected to the sixth inlet of the isomerization reactor and to the seventh outlet of the deisobutanizer.

In one aspect, the system further comprises a syngas production reactor, which is in fluid communication with the Fischer-Tropsch reactor. In one aspect, the Fischer-Tropsch reactor comprises an eighth inlet. The syngas production reactor can comprise an eighth outlet which is connected to a sixth connector, which is connected to the eighth inlet of the Fischer-Tropsch reactor.

In one aspect, the olefin separator is in fluid communication with the MTBE reactor via a seventh connector.

Isothermal and/or adiabatic fixed, moving, or fluidized bed reactors can be used as a Fischer-Tropsch reactor, which can carry out the Fischer-Tropsch process selective to the production of olefins. The Fischer-Tropsch reactor is configured to convert syngas to olefins. The isothermal and/or adiabatic fixed bed reactors are used to convert syngas to hydrocarbon products, including, olefins, paraffins, and alcohols.

The Fischer-Tropsch reactor can comprise one or more Fischer-Tropsch catalysts. Fischer-Tropsch catalysts are known in the art and can, for example, be Fe based catalysts and/or Co based catalysts and/or Ru based catalysts. Such catalysts are described in U.S. Pat. No. 4,088,671 and U.S. Pat. No. 4,207,248, which are incorporated herein by their entirety, specifically for their disclosure regarding Fischer-Tropsch catalysts.

An olefin separator is a separator that can separate olefin from paraffins and other products. The olefin separator can be a separator that cryogenically can separate olefins from paraffins. Olefin separators are known in the art and can also include distillation and membrane separation, or a combination thereof.

Deisobutanizers are known in the art. A deisobutanizer can be a fractionation column, which uses distillation separation technologies for hydrocarbon separation. Deisobutanizers are, for example, described in U.S. Pat. No. 7,638,675, U.S. Pat. No. 6,818,333, U.S. Pat. No. 6,156,950, U.S. Pat. No. 6,338,791, and U.S. Pat. No. 5,069,794, which are incorporated herein by their entirety, specifically for their disclosure regarding deisobutanizers.

A iso-butane to isobutylene reactor is a vessel that is configured to convert alkanes (i.e. paraffins) to alkenes (i.e. olefins). As such, the iso-butane to isobutylene reactor is a vessel that is configured to convert iso-butane to isobutylene. For example, the iso-butane to isobutylene reactor can be a fixed bed tubular or tube bundle reactor.

In one aspect, the iso-butane to isobutylene reactor is an iso-butane cracker. An iso-butane a reactor that is configured to heat up iso-butane to thermally break apart iso-butane to form isobutylene. An iso-butane cracker is known in the art. An iso-butane cracker can for example be a steam cracker. Iso-butane crackers and steam crackers are, for example, described in U.S. Pat. No. 5,990,370, and U.S. Pat. No. 5,785,739, which are incorporated herein by their entirety, specifically for their disclosure regarding iso-butane crackers and steam crackers.

The conversion of alkanes (i.e. paraffins) to alkenes (i.e. olefins) can be a catalytic process. In another aspect, the iso-butane to isobutylene reactor is a dehydrogenation reactor. The dehydrogenation reactor further comprises a dehydrogenation catalyst, such as, for example, a Pd or V catalyst.

In one aspect, the catalytic process can, for example, be nonoxidative as described in U.S. Pat. No. 7,417,173. The nonoxidative catalytic n-butane dehydrogenation can be carried out under heterogeneous catalysis in a fluidized bed, as described in Chem. Eng. Sci. 1992 b, 47 (9-11) 2313. Appropriately, two fluidized beds are operated in parallel, of which one is generally in the state of regeneration. The working pressure is typically from 1 to 2 bar, the dehydrogenation temperature generally from 550 to 600° C. The heat required for the dehydrogenation is introduced into the reaction system by preheating the dehydrogenation catalyst to the reaction temperature.

In another aspect, the dehydrogenation can be oxidative. Dehydrogenation catalysts such as V catalysts are, for example, described in U.S. Pat. No. 3,914,332, which is hereby incorporated by reference, specifically for the disclosure regarding oxidative catalysts.

An isomerization reactor is a vessel that is configured to isomerize alkanes, for example, a vessel that is configured to convert n-butane to i-butane. N-butane isomerization isomerization processes can use catalysts, such as a $AlCl_3$ catalyst or a Pt-alumina catalyst plus HCl. Some isomerization catalysts are sensitive to moisture, and, therefore, the n-butane isomerization processes can require feed drying. Ionic-liquid catalyst can also be used as described in U.S. 2013/0062253.

A MTBE reactor is a vessel that is configured to carry out a reaction between isobutylene and an oxygenate, such as, for example, methanol. MTBE can be produced through the reaction of isobutylene with methanol over a catalyst. In one aspect, the methanol to isobutylene ratio can be altered to maximize the conversion rate of the isobutylene. For example, as described in U.S. Pat. No. 5,414,147, the methanol to isobutylene molar ratio can be greater than 1.06 in the MTBE reaction process. In one aspect, the methanol to isobutylene molar ratio is from 1.06 to 1.2.

A syngas production reactor can produce syngas from one or more sources. Syngas can be produced from many sources, including natural gas, coal, biomass, or virtually any hydrocarbon feedstock, by reaction with steam or oxygen. For example, partial oxidation (PDX) of methane (or hydrocarbons) is a non-catalytic, large-scale process to make syngas and yields syngas with $H_2/CO$ ratio of about 2. In another example, the syngas reactor can convert natural gas into syngas. As such, the syngas production reactor can be an autothermal reforming (ATR) reactor which combines methane steam reforming and oxidation in one process. The heat needed for reforming is generated inside the reactor by oxidation of the feed gas (natural gas). ATR is also suitable for large-scale production of syngas for gas-to-liquids or large-scale methanol synthesis processes.

Optionally, in various aspects, the disclosed system can be operated or configured on an industrial scale. In one aspect, the reactors described herein can each be an industrial size reactor. For example, the Fischer-Tropsch reactor can be an industrial size reactor. In another example, the deisobutanizer can be an industrial size reactor. In yet another example, the iso-butane to isobutylene reactor can be an industrial size reactor. In yet another example, the olefin separator can be an industrial size reactor. In yet another example, the MTBE reactor can be an industrial size reactor. In yet another example, the isomerization reactor can be an industrial size reactor.

The reactors disclosed herein can have a volume of at least about 1,000 liters, about 2,000 liters, about 5,000 liters, or about 20,000 liters. For example, the reactor can have a volume from about 1,000 liter to about 20,000 liters.

In one aspect, the Fischer-Tropsch reactor can have a volume of at least about 1,000 liters, about 2,000 liters, about 5,000 liters, or about 20,000 liters. For example, Fischer-Tropsch reactor can have a volume from about 1,000 liter to about 20,000 liters.

In one aspect, the olefin separator can have a volume of at least about 1,000 liters, about 2,000 liters, about 5,000 liters, or about 20,000 liters. For example, the olefin separator can have a volume from about 1,000 liter to about 20,000 liters.

In one aspect, the deisobutanizer can have a volume of at least about 1,000 liters, about 2,000 liters, about 5,000 liters, or about 20,000 liters. For example, the deisobutanizer can have a volume from about 1,000 liter to about 20,000 liters.

In one aspect, the isomerization reactor can have a volume of at least about 1,000 liters, about 2,000 liters, about 5,000 liters, or about 20,000 liters. For example, the isomerization reactor can have a volume from about 1,000 liter to about 20,000 liters.

In one aspect, the MTBE reactor can have a volume of at least about 1,000 liters, about 2,000 liters, about 5,000 liters, or about 20,000 liters. For example, the MTBE reactor can have a volume from about 1,000 liter to about 20,000 liters.

In one aspect, the system is capable of producing at least about 25 liters, about 100 liters, about 250 liters, about 500 liters, about 1,000 liters, or about 10,000 liters, or from about 25 to about 10,000 liters of MTBE per hour.

Now referring to FIG. 1, which shows a non-limiting exemplary aspect of the system and method disclosed herein. FIG. 1 shows a system (100). The system has a syngas production reactor (102). The syngas production reactor (102) is in fluid communication with a Fischer-Tropsch reactor (104). The Fischer-Tropsch reactor (104) is in further fluid communication with an olefin separator (106). The olefin separator (106) is in further fluid communication with a deisobutanizer (108). The deisobutanizer (108) is in further fluid communication with an isomerization reactor (110) and an iso-butane to isobutylene reactor (112). The iso-butane to isobutylene reactor (such as such as an iso-butane cracker or dehydrogenator reactor) (112) is in further fluid communication with a MTBE reactor (114). The olefin separator (106) is in further fluid communication with the MTBE reactor (114). The isomerization reactor (110) is in further fluid communication with the iso-butane to isobutylene reactor (such as such as an iso-butane cracker or dehydrogenator reactor) (112). The syngas production reactor (102) can be in fluid communication with the Fischer-Tropsch reactor (104) via a sixth connector (116). The Fischer-Tropsch reactor (104) can be in further fluid communication with the olefin separator (106) via a first connector (118). The olefin separator (106) can be in further fluid communication with the deisobutanizer (108) via a second connector (120). The deisobutanizer (108) can be in further fluid communication with the isomerization reactor (110) via a fifth connector (122) and the iso-butane to isobutylene reactor (such as such as an iso-butane cracker or dehydrogenator reactor) (112) via a third connector (126). The isomerization reactor (110) is can be further fluid communication with the iso-butane to isobutylene reactor (such as such as an iso-butane cracker or dehydrogenator reactor) (112) via a seventh connector (124). The iso-butane to isobutylene reactor (112) can be in further fluid communication with the MTBE reactor (114) via a fourth connector (128). The olefin separator (106) can be in further fluid communication with the MTBE reactor (114) via a seventh connector (130).

4. Methods

Also disclosed herein is a method of producing MTBE. In one aspect, the method can be performed by the system disclosed herein.

Disclosed herein is a method comprising the steps of: a) providing a first product gas stream comprising at least about 1 wt % of a first C4 hydrocarbon product, wherein the first C4 hydrocarbon product comprises a C4 olefin hydrocarbon product comprising isobutylene and a C4 paraffin hydrocarbon product, wherein the C4 paraffin hydrocarbon product comprises n-butane and i-butane; b) separating at least a portion of the C4 olefin hydrocarbon product comprising isobutylene from the first C4 hydrocarbon product, thereby producing a second C4 hydrocarbon product; c) separating at least a portion of the n-butane from the second C4 hydrocarbon product, thereby producing a third C4 hydrocarbon product; d) isomerizing at least a portion of the separated n-butane into i-butane; e) combining at least a portion of the i-butane produced in step d) with the third C4 hydrocarbon product, thereby producing a fourth C4 hydrocarbon product; f) producing isobutylene from at least a portion of the fourth C4 hydrocarbon product; g) combining at least a portion of the separated C4 olefin hydrocarbon product comprising isobutylene and at least a portion of the isobutylene produced in step f), thereby producing a fifth C4 hydrocarbon product; and h) producing methyl tertiary butyl ether (MTBE) from at least a portion of the fifth C4 hydrocarbon product.

In one aspect, the method further comprises the step of producing the first product gas stream in Fischer-Tropsch process. The Fischer-Tropsch process can be performed in the Fischer-Tropsch reactor, as disclosed herein. In one aspect, the first product gas stream is produced from a Fischer-Tropsch process.

The first product gas stream comprising at least about 1 wt % of a first C4 hydrocarbon product, wherein the first C4 hydrocarbon product comprises a C4 olefin hydrocarbon product comprising isobutylene and a C4 paraffin hydrocarbon product. The C4 paraffin hydrocarbon product comprises n-butane and i-butane and can be produced in the Fischer-Tropsch reactor disclosed herein. In one aspect, the first product gas stream further comprises C2-C3 hydrocarbons, such as, C2-C3 olefins and paraffins. For example, the first product gas stream can further comprise at least about 1 wt % of C2-C3 olefins and paraffins. In another example, the first product gas stream can further comprise from about 1 wt % to about 50 wt %, such as from about 10 wt % to about 50 wt %, of C2-C3 olefins and paraffins.

In one aspect, the first product gas stream comprises at least about 1 wt % of the first C4 hydrocarbon product. In another aspect, the first product gas stream comprises at least about 5 wt % of the first C4 hydrocarbon product. In yet another aspect, the first product gas stream comprises at least about 10 wt % of the first C4 hydrocarbon product. In yet another aspect, the first product gas stream comprises at least about 20 wt % of the first C4 hydrocarbon product. In yet another aspect, the first product gas stream comprises at least about 30 wt % of the first C4 hydrocarbon product. In yet another aspect, the first product gas stream comprises at least about 40 wt % of the first C4 hydrocarbon product. In yet another aspect, the first product gas stream comprises at least about 50 wt % of the first C4 hydrocarbon product.

In one aspect, the first product gas stream comprises from about 1 wt % to about 80 wt % of the first C4 hydrocarbon product. In another aspect, the first product gas stream comprises from about 5 wt % to about 30 wt % of the first C4 hydrocarbon product. In another aspect, the first product gas stream comprises from about 10 wt % to about 20 wt % of the first C4 hydrocarbon product.

In one aspect, the first product gas stream comprises at least about 5 wt % of a first olefin product comprising isobutylene. In another aspect, the first product gas stream comprises at least about 10 wt % of a first olefin product comprising isobutylene. In yet another aspect, the first product gas stream comprises at least about 20 wt % of a first olefin product comprising isobutylene. In another aspect, the first product gas stream comprises at least about 30 wt % of a first olefin product comprising isobutylene. In another aspect, the first product gas stream comprises at least about 40 wt % of a first olefin product comprising isobutylene. In another aspect, the first product gas stream comprises at least about 50 wt % of a first olefin product comprising isobutylene. In another aspect, the first product gas stream comprises from about 5 wt % to about 70 wt %, such as, from about 40 wt % to about 70 wt %, of a first olefin product comprising isobutylene. The first olefin product can comprise at least about 20 wt % of C2-C8 olefins, such as from about 20 wt % to about 99 wt % of C2-C8 olefins.

The step of separating at least a portion of the C4 olefin hydrocarbon product comprising isobutylene from the first C4 hydrocarbon product, thereby producing a second C4 hydrocarbon product can be performed by the olefin separator disclosed herein. In one aspect, at least about 10 wt % of the C4 olefin hydrocarbon product comprising isobutylene in the first C4 hydrocarbon product is separated from the first C4 hydrocarbon product. In another aspect, at least about 20 wt % of the C4 olefin hydrocarbon product comprising isobutylene is separated from the first C4 hydrocarbon product. In yet another aspect, at least about 40 wt % of the C4 olefin hydrocarbon product comprising isobutylene is separated from the first C4 hydrocarbon product. In another aspect, at least about 55 wt % of the C4 olefin hydrocarbon product comprising isobutylene is separated from the first C4 hydrocarbon product. In yet another aspect, from about 10 wt % to about 95 wt %, such as from about 20 wt % to about 55 wt % of the C4 olefin hydrocarbon product comprising isobutylene is separated from the first C4 hydrocarbon product.

In one aspect, the second C4 hydrocarbon product comprises at least about 20 wt % of the C4 paraffin hydrocarbon product. For example, the second C4 hydrocarbon product comprises at least about 40 wt % of the C4 paraffin hydrocarbon product. In another example, the second C4 hydrocarbon product comprises at least about 80 wt % of the C4 paraffin hydrocarbon product. In yet another example, the second C4 hydrocarbon product comprises from about 80 wt % to about 95 wt % of the C4 paraffin hydrocarbon product.

The step of separating at least a portion of the n-butane from the second C4 hydrocarbon product, thereby producing a third C4 hydrocarbon product can be performed by the deisobutanizer disclosed herein. In one aspect, the third C4 hydrocarbon product comprises at least about 20 wt % of i-butane. In another aspect, the third C4 hydrocarbon product can comprise at least about 40 wt % of i-butane. In yet another aspect, the third C4 hydrocarbon product can comprise at least about 60 wt % of i-butane. In another aspect, the third C4 hydrocarbon product can comprise at least about 80 wt % of i-butane. In yet another aspect, the third C4 hydrocarbon product can comprise from about 80 wt % to about 99 wt % of i-butane.

The step of isomerizing at least a portion of the separated n-butane into i-butane can be performed by the isomerization reactor disclosed herein. In one aspect, at least about 20 wt % of the n-butane is isomerized to i-butane. In another aspect, at least about 50 wt % of the n-butane is isomerized to i-butane. In another aspect, at least about 75 wt % of the n-butane is isomerized to i-butane. In yet another aspect, at least about 90 wt % of the n-butane is isomerized to i-butane. In yet another aspect, from about 80 wt % to about 99 wt % of the n-butane is isomerized to i-butane.

The step of combining at least a portion of the i-butane produced in the step of isomerizing at least a portion of the separated n-butane into i-butane with the third C4 hydrocarbon product, thereby producing a fourth C4 hydrocarbon product can be done prior to entering or in the iso-butane to isobutylene reactor. In one aspect, the fourth C4 hydrocarbon product comprises at least about 20 wt % of i-butane. In another aspect, the fourth C4 hydrocarbon product can comprise at least about 50 wt % of i-butane. In another aspect, the fourth C4 hydrocarbon product can comprise at least about 75 wt % of i-butane. In another aspect, the fourth C4 hydrocarbon product can comprise at least about 90 wt % of i-butane. In yet another aspect, the fourth C4 hydrocarbon product can comprise from about 80 wt % to about 99% of i-butane.

In one aspect, the C4 hydrocarbon product comprising isobutylene comprises at least about 1 wt % of isobutylene. For example, the C4 hydrocarbon product comprising isobutylene can comprise at least about 5 wt % of isobutylene. In another aspect, the C4 hydrocarbon product comprising isobutylene can comprise at least about 10 wt % of isobutylene. In yet another aspect, the C4 hydrocarbon product comprising isobutylene can comprise at least about 25 wt % of isobutylene. In yet another aspect, the C4 hydrocarbon product comprising isobutylene can comprise at least about 50 wt % of isobutylene. In yet another aspect, the C4 hydrocarbon product comprising isobutylene can comprise at least about 75 wt % of isobutylene. In yet another aspect, the C4 hydrocarbon product comprising isobutylene can comprise at least about 85 wt % of isobutylene. In yet another aspect, the C4 hydrocarbon product comprising isobutylene can comprise at least about 90 wt % of isobutylene. In yet another aspect, the C4 hydrocarbon product comprising isobutylene can comprise at least about 95 wt % of isobutylene. In yet another aspect, the C4 hydrocarbon product comprising isobutylene can comprise from about 1 wt % to about 99%, such as, from about 20 wt % to about 99 wt % or from about 80 wt % to about 99 wt %, of isobutylene.

The step of producing isobutylene from at least a portion of the fourth C4 hydrocarbon product can be performed in the iso-butane to isobutylene reactor disclosed herein. In one aspect, at least about 50 wt % of the fourth C4 hydrocarbon product, can be converted to isobutylene. For example, at least about 70 wt % of the fourth C4 hydrocarbon product can be converted to isobutylene. In another example, at least about 90 wt % of the fourth C4 hydrocarbon product can be converted to isobutylene. In yet another example, from about 50 wt % to about 99 wt % of the fourth C4 hydrocarbon product can be converted to isobutylene.

The step of combining at least a portion of the separated C4 olefin hydrocarbon product comprising isobutylene and at least a portion of the isobutylene produced in the step of producing isobutylene from at least a portion of the fourth C4 hydrocarbon product, thereby producing a fifth C4 hydrocarbon product can be done prior to entering or in the MTBE reactor, as disclosed herein. In one aspect, the fifth C4 hydrocarbon product comprises at least about 20 wt %, such as about 50 wt %, of isobutylene. For example, the fifth C4 hydrocarbon product comprises at least about 70 wt % of isobutylene. In another example, the fifth C4 hydrocarbon product comprises at least about 90 wt % of isobutylene. In yet another example, the fifth C4 hydrocarbon product comprises from about 50 wt % to about 99 wt % of isobutylene.

The step of producing MTBE from at least a portion of the fifth C4 hydrocarbon product can be performed in the MTBE reactor, as disclosed herein. In one aspect, the step of producing MTBE comprises reacting isobutylene with an oxygenate. In another aspect, the oxygenate comprises methanol. For example, the oxygenate can be methanol.

In one aspect, at least about 60 wt % of the isobutylene is converted to MTBE. For example, at least about 80 wt % of the isobutylene can be converted to MTBE. In another example, at least about 90 wt % of the isobutylene can be converted to MTBE. In another example, at least about 99.99 wt % of the isobutylene can be converted to MTBE. In yet another aspect, from about 50 wt % to about 99.99 wt % of the isobutylene can be converted to MTBE.

In one aspect, the method converts at least about 1 wt % of the first C4 hydrocarbon product to MTBE. In another aspect, the method converts at least about 5 wt % of the first C4 hydrocarbon product to MTBE. In yet another aspect, the method converts at least about 10 wt % of the first C4 hydrocarbon product to MTBE. In yet another aspect, the method converts at least about 20 wt % of the first C4 hydrocarbon product to MTBE. In yet another aspect, the method converts at least about 40 wt % of the first C4 hydrocarbon product to MTBE. In yet another aspect, the method converts at least about 60 wt % of the first C4 hydrocarbon product to MTBE. In yet another aspect, the method converts at least about 80 wt % of the first C4 hydrocarbon product to MTBE. In yet another aspect, the method converts at least about 90 wt % of the first C4 hydrocarbon product to MTBE. In yet another aspect, the method converts from about 20 wt % to about 99 wt % of the first C4 hydrocarbon product to MTBE. In yet another aspect, the method converts from about 30 wt % to about 80 wt % of the first C4 hydrocarbon product to MTBE. In yet another aspect, the method converts from about 30 wt % to about 60 wt % of the first C4 hydrocarbon product to MTBE.

In one aspect, the method can produce at least 25 liters of MTBE per hour. In another aspect, the method can produce at least 100 liters of MTBE per hour. In yet another aspect, the method can produce at least 1,000 liters of MTBE per hour. In yet another aspect, the method can produce at least 10,000 liters of MTBE per hour. For example, the method can produce from 25 to 10,000 liters of MTBE per hour.

5. Aspects

In view of the described catalyst and catalyst compositions and methods and variations thereof, herein below are described certain more particularly described aspects of the inventions. These particularly recited aspects should not however be interpreted to have any limiting effect on any different claims containing different or more general teachings described herein, or that the "particular" aspects are somehow limited in some way other than the inherent meanings of the language and formulas literally used therein.

Aspect 1: A method comprising the steps of: a) providing a first product gas stream comprising at least about 1 wt % of a first C4 hydrocarbon product, wherein the first C4 hydrocarbon product comprises a C4 olefin hydrocarbon product comprising isobutylene and a C4 paraffin hydrocarbon product, wherein the C4 paraffin hydrocarbon product comprises n-butane and i-butane; b) separating at least a portion of the C4 olefin hydrocarbon product from the first C4 hydrocarbon product, thereby producing a second C4 hydrocarbon product; c) separating at least a portion of the n-butane from the second C4 hydrocarbon product, thereby producing a third C4 hydrocarbon product; d) isomerizing at least a portion of the separated n-butane into i-butane; e) combining at least a portion of the i-butane produced in step d) with the third C4 hydrocarbon product, thereby producing a fourth C4 hydrocarbon product; f) producing isobutylene from at least a portion of the fourth C4 hydrocarbon product; g) combining at least a portion of the separated C4 olefin hydrocarbon product and at least a portion of the isobutylene produced in step f), thereby producing a fifth C4 hydrocarbon product; and h) producing methyl tertiary butyl ether (MTBE) from at least a portion of the fifth C4 hydrocarbon product.

Aspect 2: The method of aspect 1, wherein the first product gas stream comprises at least about 5 wt % of the first C4 hydrocarbon product.

Aspect 3: The method of aspect 1, wherein the first product gas stream comprises at least about 10 wt % of the first C4 hydrocarbon product.

Aspect 4: The method of aspect 1, wherein the first product gas stream comprises from about 1 wt % to about 30 wt % of the first C4 hydrocarbon product.

Aspect 5: The method of any one of aspects 1-4, wherein the first product gas stream comprises at least about 40 wt % of a first olefin product.

Aspect 6: The method of any one of aspects 1-5, wherein the first C4 hydrocarbon product comprises at least about 20 wt % of the C4 olefin hydrocarbon product.

Aspect 7: The method of any one of aspects 1-6, wherein the first C4 hydrocarbon product comprises at least about 20 wt % of the C4 paraffin hydrocarbon product.

Aspect 8: The method of any one of aspects 1-7, wherein the second C4 hydrocarbon product comprises at least about 20 wt % of the C4 paraffin hydrocarbon product.

Aspect 9: The method of any one of aspects 1-8, wherein the third C4 hydrocarbon product comprises at least about 20 wt % of i-butane.

Aspect 10: The method of any one of aspects 1-9, wherein the fourth C4 hydrocarbon product comprises at least about 20 wt % of i-butane.

Aspect 11: The method of any one of aspects 1-10, wherein the fifth C4 hydrocarbon product comprises at least about 20 wt % of isobutylene.

Aspect 12: The method of any one of aspects 1-11, wherein the step of producing MTBE comprises reacting isobutylene with an oxygenate.

Aspect 13: The method of aspect 12, wherein the oxygenate is methanol.

Aspect 14: The aspect of any one of aspects 1-13, wherein first product gas stream is produced from a Fischer-Tropsch process converting syngas to olefins.

Aspect 15: The method of any one of aspects 1-14, wherein the method further comprises the step of producing the first product gas stream in Fischer-Tropsch process converting syngas to olefins, wherein the C4 hydrocarbon stream comprises at least about 5 wt % of iso-butylene.

Aspect 16: The method of any one of aspects 1-15, wherein the method converts at least about 5 wt % of the first C4 hydrocarbon product into MTBE.

Aspect 17: The method of any one of aspects 15-17, wherein the Fischer-Tropsch process comprises syngas produced from natural gas.

Aspect 18: A system comprising: a) a Fischer-Tropsch reactor comprising a first inlet and a first outlet; b) an olefin separator comprising a second inlet and a second outlet; c) a deisobutanizer comprising a third inlet and a third outlet; d) an iso-butane to isobutylene reactor comprising a fourth inlet and a fourth outlet; and e) MTBE reactor comprising a fifth inlet, wherein the Fischer-Tropsch reactor is in fluid communication with the olefin separator via a first connector, wherein the first connector is connected to the first outlet of the Fischer-Tropsch reactor and to the second inlet of the olefin separator, wherein the olefin separator is in fluid communication with the deisobutanizer via a second connector, wherein the second connector is connected to the second outlet of the olefin separator and to the third inlet of the deisobutanizer, wherein the deisobutanizer is in fluid communication with the iso-butane to isobutylene reactor via a third connector, wherein the third connector is connected to the third outlet of the deisobutanizer and to the fourth inlet of the iso-butane to isobutylene reactor, wherein the iso-butane to isobutylene reactor is in fluid communication with the MTBE reactor via a fourth connector, wherein the fourth connector is connected to the fourth outlet of the iso-butane to isobutylene reactor and to the fifth inlet of the MTBE reactor.

Aspect 19: The system of aspect 18, wherein the system further comprises an isomerization reactor comprising a sixth inlet and a sixth outlet, wherein the deisobutanizer further comprises a seventh outlet, wherein the isomerization reactor is in fluid communication with the deisobutanizer via fifth connector, wherein fifth connector is connected to the sixth inlet of the isomerization reactor and to the seventh outlet of the deisobutanizer.

Aspect 20: The system of aspects 18 or 19, wherein the system further comprises a syngas production reactor comprising an eight outlet, wherein the syngas production reactor is in fluid communication with the Fischer-Tropsch reactor via sixth connector, wherein the Fischer-Tropsch reactor further comprises an eighth inlet, wherein the sixth connector is connected to the eighth outlet of the syngas production reactor and to the eighth inlet of the Fischer-Tropsch reactor.

Aspect 21: The system of any one of aspects 18-20, wherein the olefin separator is in fluid communication with the MTBE reactor via a seventh connector.

Aspect 22: The system of any one of aspects 18-21, wherein the system is on an industrial scale.

What is claimed is:

1. A method comprising the steps of:
   a) providing a first product gas stream comprising at least about 1 wt % of a first C4 hydrocarbon product, wherein the first C4 hydrocarbon product comprises a C4 olefin hydrocarbon product comprising isobutylene and a C4 paraffin hydrocarbon product, wherein the C4 paraffin hydrocarbon product comprises n-butane and i-butane;
   b) separating at least a portion of the C4 olefin hydrocarbon product from the first C4 hydrocarbon product, thereby producing a second C4 hydrocarbon product;
   c) separating at least a portion of the n-butane from the second C4 hydrocarbon product, thereby producing a third C4 hydrocarbon product;
   d) isomerizing at least a portion of the separated n-butane into i-butane;
   e) combining at least a portion of the i-butane produced in step d) with the third C4 hydrocarbon product, thereby producing a fourth C4 hydrocarbon product;
   f) producing isobutylene from at least a portion of the fourth C4 hydrocarbon product;
   g) combining at least a portion of the separated C4 olefin hydrocarbon product and at least a portion of the isobutylene produced in step f), thereby producing a fifth C4 hydrocarbon product; and
   h) producing methyl tertiary butyl ether (MTBE) from at least a portion of the fifth C4 hydrocarbon product.

2. The method of claim 1, wherein the first product gas stream comprises at least about 5 wt % of the first C4 hydrocarbon product.

3. The method of claim 1, wherein the first product gas stream comprises at least about 10 wt % of the first C4 hydrocarbon product.

4. The method of claim 1, wherein the first product gas stream comprises from about 1 wt % to about 30 wt % of the first C4 hydrocarbon product.

5. The method of claim 1, wherein the first product gas stream comprises at least about 40 wt % of a first olefin product.

6. The method of claim 1, wherein the first C4 hydrocarbon product comprises at least about 20 wt % of the C4 olefin hydrocarbon product.

7. The method of claim 1, wherein the first C4 hydrocarbon product comprises at least about 20 wt % of the C4 paraffin hydrocarbon product.

8. The method of claim 1, wherein the second C4 hydrocarbon product comprises at least about 20 wt % of the C4 paraffin hydrocarbon product.

9. The method of claim 1, wherein the third C4 hydrocarbon product comprises at least about 20 wt % of i-butane.

10. The method of claim 1, wherein the fourth C4 hydrocarbon product comprises at least about 20 wt % of i-butane.

11. The method of claim 1, wherein the fifth C4 hydrocarbon product comprises at least about 20 wt % of isobutylene.

12. The method of claim 1, wherein the step of producing MTBE comprises reacting isobutylene with an oxygenate.

13. The method of claim 12, wherein the oxygenate is methanol.

14. The method of claim 1, wherein the method further comprises the step of producing the first product gas stream in Fischer-Tropsch process converting syngas to olefins, wherein the C4 hydrocarbon stream comprises at least about 5 wt % of iso-butylene.

15. The method of claim 1, wherein the method converts at least about 5 wt % of the first C4 hydrocarbon product into MTBE.

16. A system comprising:
   a) Fischer-Tropsch reactor comprising a first inlet and a first outlet;
   b) an olefin separator comprising a second inlet and a second outlet;
   c) a deisobutanizer comprising a third inlet and a third outlet;
   d) an iso-butane to isobutylene reactor comprising a fourth inlet and a fourth outlet; and
   e) MTBE reactor comprising a fifth inlet, wherein the Fischer-Tropsch reactor is in fluid communication with the olefin separator via a first connector, wherein the first connector is connected to the first outlet of the Fischer-Tropsch reactor and to the second inlet of the olefin separator, wherein the olefin separator is in fluid communication with the deisobutanizer via a second connector, wherein the second connector is connected to the second outlet of the olefin separator and to the third inlet of the deisobutanizer, wherein the deisobutanizer is in fluid communication with the iso-butane to isobutylene reactor via a third connector, wherein the third connector is connected to the third outlet of the deisobutanizer and to the fourth inlet of the iso-butane to isobutylene reactor, wherein the iso-butane to isobutylene reactor is in fluid communication with the MTBE reactor via a fourth connector, wherein the fourth connector is connected to the fourth outlet of the iso-butane to isobutylene reactor and to the fifth inlet of the MTBE reactor.

17. The system of claim 16, wherein the system further comprises an isomerization reactor comprising a sixth inlet and a sixth outlet, wherein the deisobutanizer further comprises a seventh outlet, wherein the isomerization reactor is in fluid communication with the deisobutanizer via fifth connector, wherein fifth connector is connected to the sixth inlet of the isomerization reactor and to the seventh outlet of the deisobutanizer.

18. The system of claim 16 or 17, wherein the system further comprises a syngas production reactor comprising an eight outlet, wherein the syngas production reactor is in fluid communication with the Fischer-Tropsch reactor via sixth connector, wherein the Fischer-Tropsch reactor further comprises an eighth inlet, wherein the sixth connector is connected to the eighth outlet of the syngas production reactor and to the eighth inlet of the Fischer-Tropsch reactor.

19. The system of claim 16, wherein the olefin separator is in fluid communication with the MTBE reactor via a seventh connector.

20. The system of claim 16, wherein the system is on an industrial scale.

* * * * *